(12) United States Patent
Shin et al.

(10) Patent No.: US 9,102,755 B2
(45) Date of Patent: Aug. 11, 2015

(54) HIGHLY STABILIZED EPIDERMAL GROWTH FACTOR MUTANTS

(71) Applicant: PnP Biopharm Co., Ltd., Seoul (KR)

(72) Inventors: Hang-Cheol Shin, Seoul (KR); Dong-Hwan Kim, Seoul (KR); Ha A Rin Chun, Jeollanam-do (KR); Seung-Taek Sun, Seoul (KR)

(73) Assignee: PnP Biopharm Co., Ltd., Seoul (KR)

( * ) Notice: Subject to any disclaimer, the term of this patent is extended or adjusted under 35 U.S.C. 154(b) by 0 days.

(21) Appl. No.: 14/172,310

(22) Filed: Feb. 4, 2014

(65) Prior Publication Data

US 2015/0031611 A1    Jan. 29, 2015

(30) Foreign Application Priority Data

Jul. 23, 2013  (KR) .................. 10-2013-0086773

(51) Int. Cl.
*C07K 14/485*    (2006.01)

(52) U.S. Cl.
CPC .................................. *C07K 14/485* (2013.01)

(58) Field of Classification Search
CPC .................................................. C07K 14/485
See application file for complete search history.

(56) References Cited

U.S. PATENT DOCUMENTS 8,247,531 B2 *  8/2012  Cochran et al. .............. 530/324

FOREIGN PATENT DOCUMENTS

KR           960013439 B1    10/1996
WO    WO 2010/020811      *   2/2010

OTHER PUBLICATIONS

Carlos George-Nascimento et al., "Replacement of a Labile Aspartyl Residue Increases the Stability of Human Epidermal Growth Factor", Biochemistry, 1990, American Chemical Society, vol. 29, No. 41, pp. 9584-9591.
Ji Won Park et al., "Epidermal Growth Factor (EGF) receptor targeted delivery of PEGylated Adenovirus", Biochemical and Biophysical Research Communications, 2008, vol. 366, Elsevier Inc., pp. 769-774.

* cited by examiner

*Primary Examiner* — Marianne P Allen
(74) *Attorney, Agent, or Firm* — Baker & Hostetler LLP

(57) ABSTRACT

There are provided mutants prepared by changing a DNA base sequence and an amino acid sequence of an epidermal growth factor (EGF), in which a mutant EGF protein has excellent thermal stability and stability even in the state of an aqueous solution, and a gene encoding the protein are provided; a recombinant vector including the gene and a microorganism transformed by the recombinant vector are provided; a method of preparing the mutant EGF protein is provided; a cosmetic composition for accelerating the growth of skin cell and skin regeneration, including the protein, the gene, or the recombinant vector, is provided; and by preparing a product using the EGF mutant according to the present invention, it is possible to produce functional cosmetics, in which the activity thereof is maintained even during a distribution and storage process unlike the conventional wild-type EGF product.

1 Claim, 7 Drawing Sheets

HIGHLY STABILIZED EPIDERMAL GROWTH FACTOR MUTANTS

CROSS-REFERENCE TO RELATED APPLICATIONS

This application is based on and claims priority from Korean Patent Application No. 10-2013-0086773, filed on Jul. 23, 2013, with the Korean Intellectual Property Office, the disclosure of which is incorporated herein in its entirety by reference.

SEQUENCE LISTING

The instant application contains a Sequence Listing which has been submitted electronically in ASCII format and is hereby incorporated by reference in its entirety. Said ASCII copy, created on Mar. 20, 2015, is named 087248.001880_SL.txt and is 23,162 bytes in size.

TECHNICAL FIELD

The present invention relates to mutants having mutated base sequence and amino acid sequence of DNA of an epidermal growth factor (EGF). More particularly, the present invention relates to mutants of an EGF, in which its thermal stability and solubility to an aqueous solution are increased and also its activity is maintained by using a substitution method into hydrophilic residues and a disulfide bond.

BACKGROUND

An epidermal growth factor (EGF) has been first found by S. Cohen in U.S.A. in 1953. An EGF derived from human is polypeptide composed of 53 amino acids, which has a molecular weight of 6,045 Dalton and three disulfide bonds. It is known that since the EGF has activities such as suppression of gastric acid secretion, acceleration of cell growth, and acceleration of mitosis to various cells including a mesenchymal cell and an epithelial cell of mammals, the EGF can be used as an agent for treating a stomach ulcer and an agent for treating wound of skin or cornea. Recently, the EGF is being used as an agent for treating wound and the damaged stomach walls, and also is being recognized as a medicine for diabetic foot ulcer that mainly occurs in a diabetic.

However, in recent years, the field that uses an EGF the most is the field of cosmetics. With advancing years, the concentrations of growth factors, such as an EGF, are lower and the functions of cell recycle and cell division are deteriorated, thereby accelerating the ageing process, for example, forming wrinkles and reducing elasticity. In general, for the skin after 25 years of age, the growth factors are decreased, and thus metabolism or cell recycle ability is gradually getting late, thereby forming wrinkles. The cycle of skin regeneration for healthy young people is about 4 weeks, but the cycle of skin regeneration for the skin after 25 years of age is 6 weeks, that is late. Therefore, the generation ability of skin cells is decreased and stratum corneum is thickened, thereby proceeding the ageing process. An EGF is a factor for accelerating the growth of an epithelial cell, and it is known that the growth of an epithelial cell is accelerated by inducing the growth and division of cells, especially, an epithelial cell and skin cell of mammal by transferring signal through an EGF receptor present on a cell membrane. Therefore, when an EGF is applied to the skin using cosmetics, the EGF plays a key role for the skin regeneration, for example, the proliferations of an epithelial cell and hypodermal cell are accelerated, the cell proliferation of fibroblasts synthesizing collagen that is a component constituting the dermis, vascularization of the damaged skin part is accelerated, the secretions of other regeneration stimulating factors are induced, the skin tissue takes its course in arrangement, the synthesis of fibronectin that is a material allowing a net to be formed is accelerated, and the scar in the wounded area is minimized. Therefore, the EGF can help the original functions of the skin that are deteriorated with advancing years and can accelerate the growth of the new skin cells. For this reason, the EGF was designated on International Cosmetic Ingredient Dictionary (ICID) of The Cosmetic, Toiletry and Fragrance Association (CTFA), and recently, also was approved as a cosmetic raw material at Korea Food & Drug Administration. Therefore, the EGF can be formally used as a cosmetic raw material at home and abroad.

For this reason, an EGF is tried to use in many fields. However, in early days, the EGF is obtained through purification among various growth factors derived during a generation process of stem cells, and thus its purity and activity are low, the productivity thereof is low, and it is produced through a high cost process. Therefore, the application thereof is limited due to a high cost. However, recently, it is possible to produce an EGF in bulk with low cost by producing the same protein as an EGF in the human body from microorganisms by a genetic engineering technique, and then purely isolating only an EGF using a protein isolation and purification technique.

However, the EGF thus produced is sensitive when it is present at a relatively high temperature and in an aqueous solution, and thus the activity thereof is greatly deteriorated in a general product state or under a distribution environment. Therefore, in order to use the EGF as a cosmetic raw material, the need to stabilize the EGF has been proposed. Accordingly, it is needed that an EGF mutant capable of replacing for the conventional EGF is prepared thereby providing an EGF having excellent stability while the activity thereof is maintained. Currently, a study on an EGF mutant is focused on the development of the mutant exhibiting the higher activity rather than the stability. As a case of increasing stability, there is a method of increasing a degree of EGF stability through secretion suppression by substituting unstable aspartic acid with other amino acids, but a follow-up study is not progressed (Nascimento, G. C. et al., Biochemistry. 29:9584-9591, 1990). Otherwise, there is a case of increasing stability by attaching other materials to an EGF, such as albumin fusion epidermal growth factor, PEG-EGF (Park, J. W. et al., Biochem Biophys Res Commun. 366:769-774, 2008). However, for such a case, there is a problem in that the size of the whole proteins becomes larger, and thereby it is difficult to be absorbed to the skin. Therefore, it is important to develop an EGF mutant having increased stability by only the change of amino acid in the EGF without changing the size of protein.

Meanwhile, Korean Patent No. 10-0110123 relates to a stable epidermal growth factor (EGF) composition, in which the biological activity thereof can be maintained and also the EGF composition is stable biologically, chemically, and physically by adding the additives selected from phenol, polyethylene glycol, fatty acid salts, and the like to an epidermal growth factor (EGF). However, it does not disclose the EGF mutant having high stability, which is produced by changing the amino acid sequence in the EGF according to the present invention.

SUMMARY

An object of the present invention is to provide a mutant EGF protein having excellent stability in an aqueous solution state and excellent thermal stability, in which the amino acid sequence of an epidermal growth factor (EGF) protein is substituted.

Another object of the present invention is to provide a gene encoding the mutant epidermal growth factor (EGF) protein.

Still another object of the present invention is to provide a recombinant vector including the gene and a microorganism transformed by the recombinant vector.

Still another object of the present invention is to provide a method of preparing the mutant epidermal growth factor (EGF) protein.

Still another object of the present invention is to provide a cosmetic composition including the protein, the gene, or the recombinant vector, for the growth of skin cells and acceleration of skin regeneration.

In order to achieve the above objects, the present inventors prepared mutants through a homology alignment method between species and a tertiary structure of an EGF, a protein molecule modeling using a computer, a selection of the sites not relating to an active site of an EGF, and a systematic mutation experiment. As a first method, stability against the precipitation generated due to the impulse of hydrophobic residues on a surface by substituting the hydrophobic residues with hydrophilic residues on the surface of an EGF is increased. As a second method, the stability is increased by using a method of causing a loop entropy reduction through additionally disulfide bond by substituting two residues adjacent to each other in a loop of the EGF with cysteine. Therefore, the present invention is completed.

The present invention provides a mutant epidermal growth factor (EGF) protein including an amino acid sequence having at least one substituted amino acid selected from the group consisting of the following 1) to 13), for the amino acid sequence of an epidermal growth factor (EGF) protein as set forth in SEQ ID NO:1.

1) Substitution of serine, fourth-amino acid, with arginine or glutamic acid;
2) Substitution of leucine, eighth-amino acid, with serine or proline;
3) Substitution of leucine, fifteenth-amino acid, with cysteine;
4) Substitution of valine, nineteenth-amino acid, with serine, glutamic acid, aspartic acid, or lysine;
5) Substitution of alanine, $25^{th}$-amino acid, with serine;
6) Substitution of leucine, $26^{th}$-amino acid, with serine;
7) Substitution of valine, $34^{th}$-amino acid, with serine, glutamic acid, aspartic acid, or lysine;
8) Substitution of valine, $35^{th}$-amino acid, with serine, glutamic acid, aspartic acid, or lysine;
9) Substitution of isoleucine, $38^{th}$-amino acid, with serine, cysteine, glutamic acid, or aspartic acid;
10) Substitution of arginine, $41^{st}$-amino acid, with cysteine;
11) Substitution of aspartic acid, $46^{th}$-amino acid, with cysteine;
12) Substitution of lysine, $48^{th}$-amino acid, with arginine; and
13) Substitution of tryptophan, $50^{th}$-amino acid, with serine, histidine, or glutamic acid.

In detail, the protein includes at least one substituted amino acid sequence selected from the group consisting of the substitution of leucine, eighth-amino acid, with serine; the substitution of isoleucine, $38^{th}$-amino acid, with serine or cysteine; and the substitution of aspartic acid, $46^{th}$-amino acid, with cysteine, in the amino acid sequence as set forth in SEQ ID NO:1.

In more detail, the protein is an amino acid sequence as set forth in SEQ ID NO:2. SEQ ID NO:2 is an amino acid sequence prepared by substituting leucine, eighth-amino acid, with serine, by substituting isoleucine, $38^{th}$-amino acid, with cysteine, and by substituting aspartic acid, $46^{th}$-amino acid, with cysteine, in the amino acid sequence as set forth in SEQ ID NO:1.

In addition, the present invention provides a gene encoding the mutant epidermal growth factor (EGF). Preferably, the gene has an amino acid sequence as set forth in SEQ ID NO:4. SEQ ID NO:4 is a base sequence preferred by substituting CTG (codon of leucine), $22^{nd}$ to $24^{th}$-base sequence, with AGC (codon of serine), by substituting ATC (codon of isoleucine), 112nd to $114^{th}$-base sequence, with TGC (codon of cystein), and by substituting GAC (codon of aspartic acid), $136^{th}$ to $138^{th}$-base sequence, with TGC (codon of cystein), in SEQ ID NO:3 representing a base sequence of a wild-type EGF gene.

In addition, the present invention provides a recombinant vector including the gene.

According to the present invention, the "vector" means a DNA molecule, which can be replicated by itself and used for delivering a clone gene (or other fragments of the clone DNA). It may include all kinds of the general vectors, such as a plasmid vector, a cosmid vector, a bacteriophage vector, and a virus vector. A plasmid vector is preferable.

In addition, the present invention provides a recombinant microorganism transformed by the recombinant vector.

The microorganism that can be used as a host cell capable of being transformed is not particularly limited. Examples of the microorganism include various microorganisms, such as *Escherichia coli, Rhodococcus, Pseudomonas, Streptomyces, Staphylococcus, Syfolobus, Thermoplasma,* and *Thermoproteus. Escherichia coli* BL21 (DE3) is preferable, but examples thereof may include *Escherichia coli* XL1-blue, *Escherichia coli* JM109, *Escherichia coli* DH series, *Escherichia coli* TOP10, *Escherichia coli* HB101, and the like. However, the present invention is not limited thereto.

For transforming the vector including the mutant EGF gene according to the present invention to a host cell, all kinds of the method of introducing nucleic acid into a cell for a transformation of host cell are included, and the proper technique may be selected and then performed according to a host cell. Such a method includes electroporation, plasmogamy, calcium phosphate ($CaPO_4$) precipitation, calcium chloride ($CaCl_2$), and the like, but the present invention is not limited thereto.

In addition, the present invention provides a method of preparing a mutant epidermal growth factor (EGF) protein, in which the method includes preparing the recombinant vector; transforming *Escherichia Coli* with the recombinant vector; expressing a mutant EGF protein by culturing the transformed *Escherichia Coli*; and collecting the expressed protein.

In addition, the present invention provides a cosmetic composition including the protein, the gene, or the recombinant vector, for accelerating the growth of skin cell and skin regeneration.

The components included in the cosmetic composition of the present invention may include the components that are generally used for a cosmetic composition, for example, the general adjurvants such as an antioxidant, a stabilizer, a solvent, vitamins, pigment, and flavorings, and a carrier. In addition, the cosmetic composition may further include a skin absorption accelerator in order to improve the effect thereof.

The cosmetic composition according to the present invention may be formulated in any kinds of forms that are generally prepared in the prior art, and for example, may be formulated in a type of a solution, suspension, emulsion, paste, gel, cream, lotion, powder, soap, oil, powder foundation, emulsion foundation, wax foundation, or spray. More specifically, it may be formulated in a type of a skin lotion, nutrients, massage creams, essence, eye cream, cleansing cream, cleansing foams, cleansing water, pack, spray, or powder.

The items related to the genetic engineering technique used for the present invention can refer to the documents such as Sambrook (Sambrook, et al. Molecular Cloning, A Laboratory Manual, Cold Spring Harbor laboratory Press, Cold Spring Harbor, N. Y. (2001)) and the documents such as Frederick (Frederick M. Ausubel et al., Current protocols in molecular biology volume 1,2,3, John Wiley & Sons, Inc. (1994)).

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Example 1

Construction of pSSB-EGF Plasmid Including Human EGF cDNA

1. Experimental Materials pET21a as a protein expression vector and BL21 (DE3) Rosetta (DE3) as an *E. coli* strain were purchased from Novagen, and Top10 was used as an *E. coli* strain for cloning. All the restriction enzymes used at the time of a gene recombination were products of NEB (New England Biolabs), and T4 DNA ligase was used as ligase prepared by Roche. Ex taq DNA polymerase used at the time of PCR was a product prepared by Takara, and pfuUltra™ HF DNA polymerase used for a point mutation was a product prepared by Agilent. DNA gel extraction kit and plasmid mini prep kit were products prepared by Cosmogenetech Co., Ltd. In addition, primers were prepared by Cosmogenetech Co., Ltd., and a DNA sequencing was performed in Cosmogenetech Co., Ltd.

2. Results

The DNA encoding an EGF was prepared through a polymerase chain reaction method using the primers having the following base sequences using a human mononuclear cell cDNA library as a template. The base sequences of the primers used are as follows. Sense primer 5'-GCTGTTCATATGAACAGCGATAGCGAATGC-3' (SEQ ID NO:5) and Antisense primer 3'-TAATAAAAGCTTTTATTAGCGCAGTTCCCACCA-5'. (SEQ ID NO:6).

Figure 1:
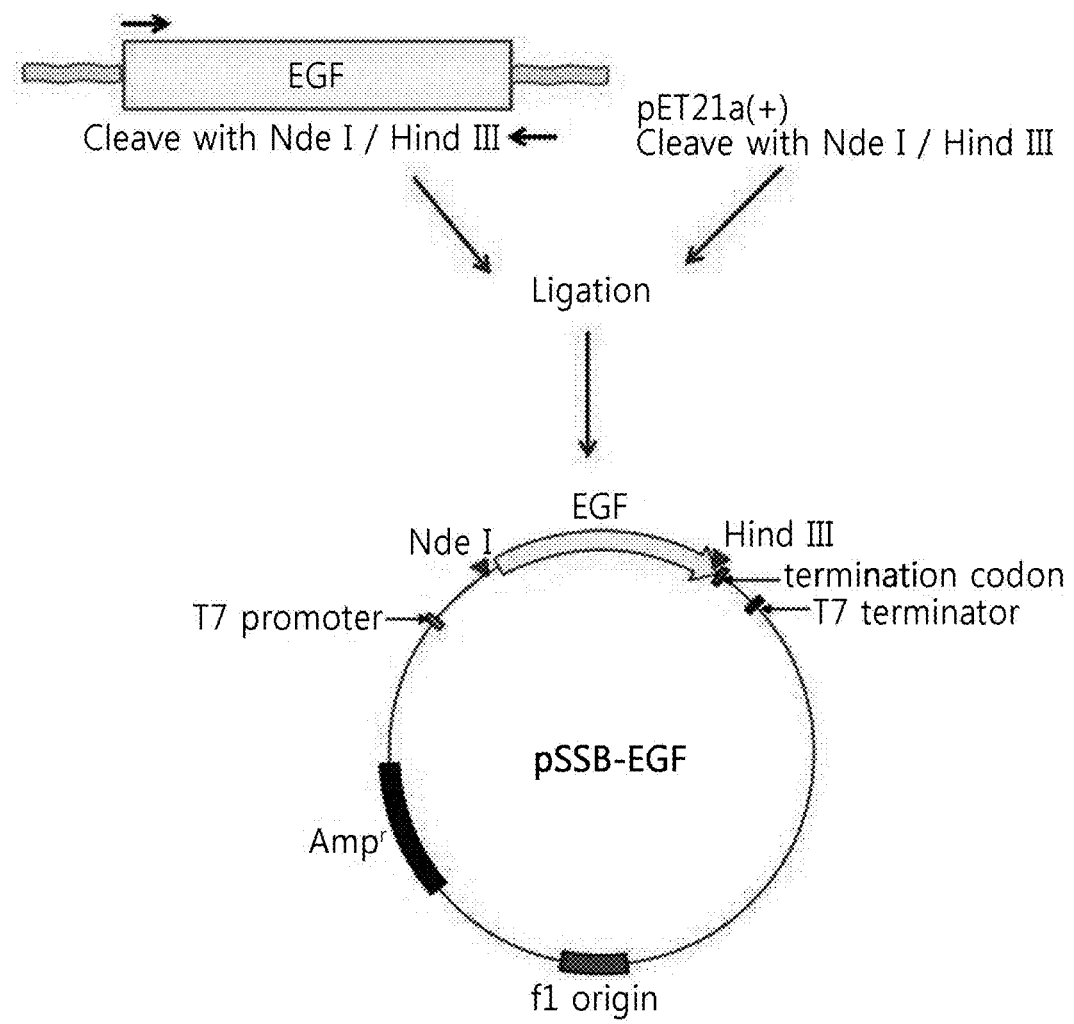
FIG. 1 exhibits an outline of preparing a plasmid pSSB-EGF.
Figure 2A:
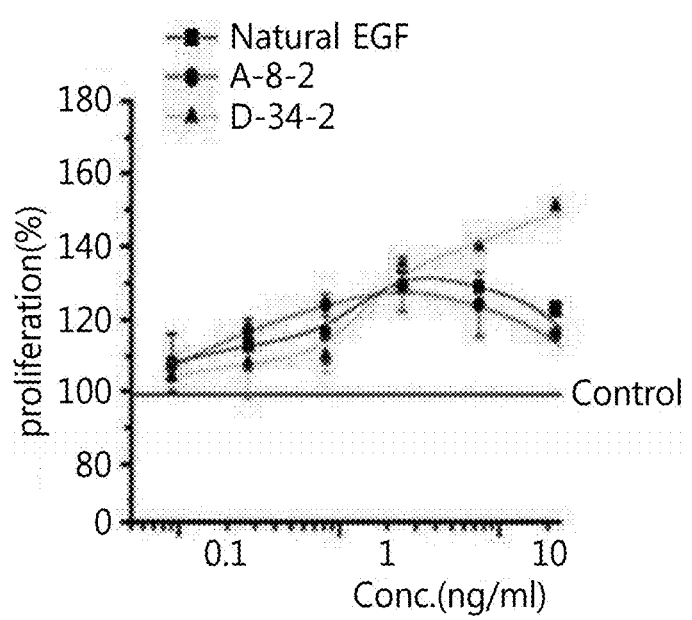
FIG. 2A-D are graphs comparing the abilities of cell proliferation between a wild-type EGF and a EGF mutant produced according to the present invention, in which most EGF mutants have the similar ability of cell proliferation as the wild-type EGF.
Figure 2B:
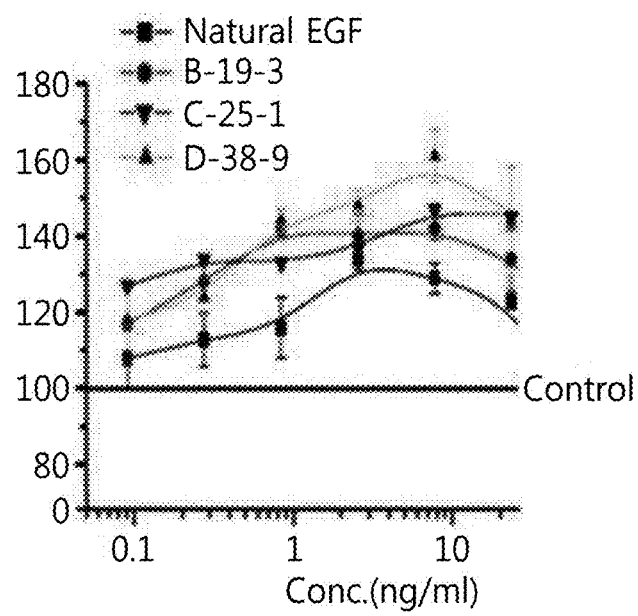
Figure 2C:
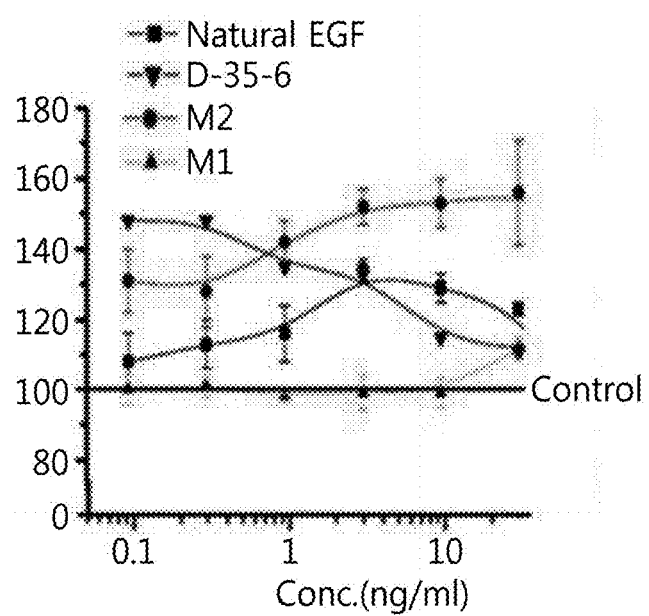
Figure 2D:
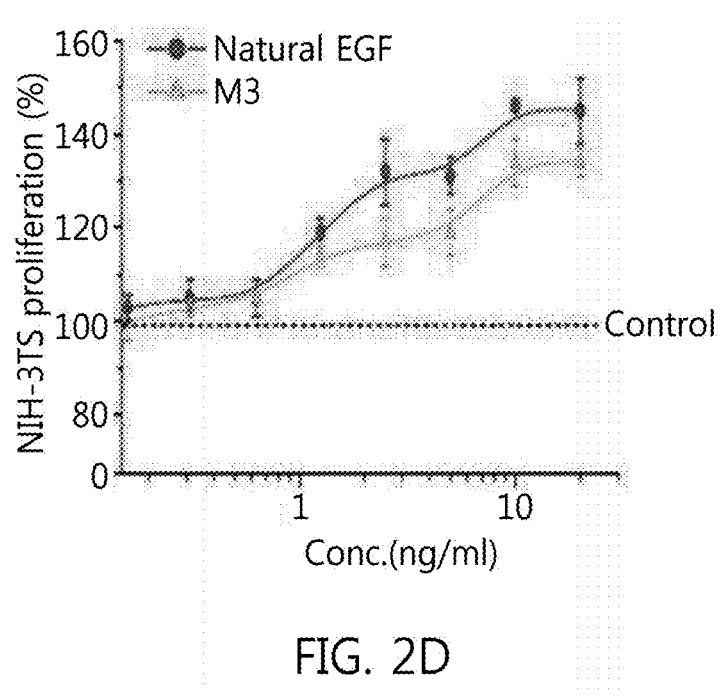

As illustrated in FIG. 1, 1 µg of an amplified DNA fragment was dissolved in a 50 µl TE (pH 8.0) solution, and then was mixed with 2 unit of Nde I (manufactured by NEB) and 2 unit of Hind III (manufactured by NEB). And then, the mixture thus obtained was reacted at a temperature of 37° C. for 2 hours to have Nde I restriction enzyme site at 5'-end and Hind III restriction enzyme site at 3'-end. Only DNA was purified by using a DNA purification kit (manufactured by GeneAll). And then, 20 ng of the DNA fragment thus obtained was mixed in 10 µl of TE (pH 8.0) solution along with 20 ng of pET21a (+) plasmid (manufactured by Novagen) prepared after being treated with Nde I and Hind III, respectively, using the same method. Since then, 1 unit of T4 DNA ligase (manufactured by NEB) was added thereto, and then reacted at a temperature of 16° C. for 4 hours to be bonded. The plasmid thus prepared is called pSSB-EGF.

Example 2

Preparation and Purification of *E. coli* Transformant of Human EGF

*E. coli* BL21 (DE3) was transformed through a heat shock using an expression plasmid pSSB-EGF. After transforming, the colony formed on a solid medium having resistance against ampicillin was selected, and then inoculated into a 10 ml of LB medium (LB/ampicillin). After culturing at a temperature of 37° C. for 12 hours, the medium cultured was mixed with 100% glycerol in a ratio of 1:1, and then the stock thus obtained was stored at a temperature of −70° C.

The stock prepared as described above was inoculated in a 10 ml of LB medium (LB/ampicillin), and then cultured for 12 hours. Since then, the medium cultured was transferred into a 500 ml of LB medium (LB/ampicillin), and then when an absorbance at 600 nm was O.D. 0.4 to 0.5, IPTG (isopropyl-1-thio-β-D-galactopyranoside) was added to the medium to be a final concentration of 0.5 mM. The medium thus obtained was shake-cultured at a temperature of 37° C. and a rate of 200 rpm for 4 hours, and then centrifuged at 8000 rpm for 10 minutes to obtain an *E. coli* pellet. Such a pellet was suspended in a 25 ml of 50 mM tris (pH 8.0) buffer solution, and then the cells were sonicated by using an ultrasonification method.

The cell lysis solution sonicated through an ultrasonification was centrifuged at a temperature of 4° C. and 13000 rpm for 15 minutes. The supernatant was thrown away, and the pellet thus obtained was taken. The pellet was washed twice with third distilled water. To the obtained washed pellet, 6 M guanidine-HCl and 50 mM tris (pH 8.0) were added and then thoroughly stirred for about 1 hour. Since then, in order to remove the guanidine-HCl, the stirred pellet was dialyzed twice for 6 hours in 50 mM tris (pH 8.0), and then centrifuged at 13000 rpm for 15 minutes to divide the supernatant and pellet. By using the supernatant obtained after dialyzing, an EGF was quantified using a Bradford method, and then the EGF was treated with β-mercaptoethanol in an equivalent of 4.5 with respect to the EGF to reshuffle it at room temperature for 16 hours or more. After completing the reaction, the filtering was performing using 0.2 µm filter, and then the pH thereof was acidified to be pH 3.0 or less using hydrochloric acid. The solution thus obtained was purified by using a HPLC (high performance liquid chromatography) and ODS-AQ pack column. At this time, as a purification condition, the solution A of 0.1% trifluoroacetic acid and the solution B of 0.1% trifluoroacetic acid including 90% acetonitrile were flowed in a straight grade from 0% B to 100% B in a rate of 0.6 ml/min to elute. Since then, the fraction including the EGF protein of about 6 KDa size was collected. At this time, the amounts of EGFs obtained were 0.3 to 0.5 mg, respectively, and purities thereof were 98% or higher.

Example 3

Construction of pSSB-EGF Mutant Plasmid

The pSSB-EGF mutant plasmids were prepared by using a PCR with two complementary primers corresponding to the respective mutants using pfuUltra™ HF DNA polymerase to the wild type pSSB-EGF plasmids, as a template. And then, the wild-type pSSB-EGF plasmids that were templates were cleaved using Dpn I, and then transformed into an *E. coli* Top 10 by using a heat shock. After transforming, the colony having resistance against ampicillin, which was generated in a solid medium, was selected and then inoculated in a 10 ml of LB medium (LB/ampicillin). After culturing at a temperature of 37° C. for 16 hours, the DNA prep was performed, and then in the DNA thus obtained, pSSB-EGF mutant plasmid was confirmed through sequencing. At this time, the base sequences of the primers used are as follows.

(1) Substitution of AGC, codon of fourth serine, with GAA, codon of glutamic acid, in SEQ ID NO: 1
Sense primer
(SEQ ID NO: 7)
5'-AAC AGC GAT GAA GAA TGC CCG CTG AGC-3'
Antisense primer
(SEQ ID NO: 8)
3'-TTG TCG CTA CTT CTT ACG GGC GAC TCG-5'

(2) Substitution of CTG, codon of eighth leucine, with AGC, codon of serine, or CCG, codon of proline, in SEQ ID NO: 1
Sense primer
(SEQ ID NO: 9)
5'-GAT AGC GAA TGC CCG AGC AGC CAT GAT GGC TAT-3'
Antisense primer
(SEQ ID NO: 10)
3'-CTA TCG CTT ACG GGC TCG TCG GTA CTA CCG ATA-5'

(3) Substitution of CTG, codon of 15$^{th}$ leucine, with TGC, codon of cysteine, in SEQ ID NO: 1
Sense primer
(SEQ ID NO: 11)
5'-CAT GAT GGC TAT TGC TGC CAT GAT GGT GTG TGC-3'
Antisense primer
(SEQ ID NO: 12)
3'-GTA CTA CCG ATA ACG ACG GTA CTA CCA CAC ACG-5'

(4) Substitution of GTG, codon of 19$^{th}$ valine, with AGC, codon of serine, GAA, codon of glutamic acid, GAT, codon of aspartic acid, or AAA, codon of lysine, in SEQ ID NO: 1
Sense primer
(SEQ ID NO: 13)
5'-TGC CTG CAT GAT GGT AGC TGC ATG TAT ATT GAA-3'
Antisense primer
(SEQ ID NO: 14)
3'-ACG GAC GTA CTA CCA TCG ACG TAC ATA TAA CTT-5'

Sense primer
(SEQ ID NO: 15)
5'-TGC CTG CAT GAT GGT GAA TGC ATG TAT ATT GAA-3'
Antisense primer
(SEQ ID NO: 16)
3'-ACG GAC GTA CTA CCA ATT ACG TAC ATA TAA CTT-5'

Sense primer
(SEQ ID NO: 17)
5'-TGC CTG CAT GAT GGT GAT TGC ATG TAT ATT GAA-3'
Antisense primer
(SEQ ID NO: 18)
3'-ACG GAC GTA CTA CCA CTA ACG TAC ATA TAA CTT-5'

-continued

Sense primer (SEQ ID NO: 19)
5'-TGC CTG CAT GAT GGT AAA TGC ATG TAT ATT GAA-3'

Antisense primer (SEQ ID NO: 20)
3'-ACG GAC GTA CTA CCA TTT ACG TAC ATA TAA CTT-5'

(5) Substitution of GCA, codon of 25th alanine, with AGC, codon of serine, in SEQ ID NO: 1

Sense primer (SEQ ID NO: 21)
5'-TGC ATG TAT ATT GAA AGC TTG GAC AAG TAT GCA-3'

Antisense primer (SEQ ID NO: 22)
3'-ACG TAC ATA TAA CTT TCG AAC CTG TTC ATA CGT-5'

(6) Substitution of CTG, codon of 26th leucine, with AGC, codon of serine, in SEQ ID NO: 1

Sense primer (SEQ ID NO: 23)
5'-ATG TAT ATT GAA AGC TTG GAC AAG TAT GCA TGC-3'

Antisense primer (SEQ ID NO: 24)
3'-TAC ATA TAA CTT TCG AAC CTG TTC ATA CGT ACG-5'

(7) Substitution of GTG, codon of 34th valine, with AGC, codon of serine, GAA, codon of glutamic acid, GAT, codon of aspartic acid, or AAA, codon of lysine, in SEQ ID NO: 1

Sense primer (SEQ ID NO: 25)
5'-TAT GCA TGC AAC TGT AGC GTT GGC TAC ATC GGC-3'

Antisense primer (SEQ ID NO: 26)
3'-ATA CGT ACG TTG ACA TCG CAA CCG ATG TAG CCG-5'

Sense primer (SEQ ID NO: 27)
5'-TAT GCA TGC AAC TGT GAA GTT GGC TAC ATC GGC-3'

Antisense primer (SEQ ID NO: 28)
3'-ATA CGT ACG TTG ACA CTT CAA CCG ATG TAG CCG-5'

Sense primer (SEQ ID NO: 29)
5'-TAT GCA TGC AAC TGT GAT GTT GGC TAC ATC GGC-3'

Antisense primer (SEQ ID NO: 30)
3'-ATA CGT ACG TTG ACA CTA CAA CCG ATG TAG CCG-5'

Sense primer (SEQ ID NO: 31)
5'-TAT GCA TGC AAC TGT AAA GTT GGC TAC ATC GGC-3'

Antisense primer (SEQ ID NO: 32)
3'-ATA CGT ACG TTG ACA TTT CAA CCG ATG TAG CCG-5'

(8) Substitution of GTG, codon of 35th valine, with AGC, codon of serine, GAA, codon of glutamic acid, GAT, codon of aspartic acid, or AAA, codon of lysine, in SEQ ID NO: 1

Sense primer (SEQ ID NO: 33)
5'-GCA TGC AAC TGT GTT AGC GGC TAC ATC GGC GAG-3'

Antisense primer (SEQ ID NO: 34)
3'-CGT ACG TTG ACA CAA TCG CCG ATG TAG CCG CTC-5'

Sense primer (SEQ ID NO: 35)

5'-GCA TGC AAC TGT GTT GAA GGC TAC ATC GGC GAG-3'

Antisense primer (SEQ ID NO: 36)

3'-CGT ACG TTG ACA CAA CTT CCG ATG TAG CCG CTC-5'

Sense primer (SEQ ID NO: 37)

5'-GCA TGC AAC TGT GTT GAT GGC TAC ATC GGC GAG-3'

Antisense primer (SEQ ID NO: 38)

3'-CGT ACG TTG ACA CAA CTA CCG ATG TAG CCG CTC-5'

Sense primer (SEQ ID NO: 39)

5'-GCA TGC AAC TGT GTT AAA GGC TAC ATC GGC GAG-3'

Antisense primer (SEQ ID NO: 40)

3'-CGT ACG TTG ACA CAA TTT CCG ATG TAG CCG CTC-5'

(9) Substitution of ATC, codon of 38$^{th}$ isoleucine, with AGC, codon of serine, TGC, codon of cysteine, GAA, codon of glutamic acid, or GAT, codon of aspartic acid, in SEQ ID NO: 1

Sense primer (SEQ ID NO: 41)

5'-TGT GTT GTT GGC TAC AGC GGC GAG CGT TGC CAG-3'

Antisense primer (SEQ ID NO: 42)

3'-ACA CAA CAA CCG ATG TCG CCG CTC GCA ACG GTC-5'

Sense primer (SEQ ID NO: 43)

5'-TGT GTT GTT GGC TAC TGC GGC GAG CGT TGC CAG-3'

Antisense primer (SEQ ID NO: 44)

3'-ACA CAA CAA CCG ATG ACG CCG CTC GCA ACG GTC-5'

Sense primer (SEQ ID NO: 45)

5'-TGT GTT GTT GGC TAC GAA GGC GAG CGT TGC CAG-3'

Antisense primer (SEQ ID NO: 46)

3'-ACA CAA CAA CCG ATG CTT CCG CTC GCA ACG GTC-5'

Sense primer (SEQ ID NO: 47)

5'-TGT GTT GTT GGC TAC GAT GGC GAG CGT TGC CAG-3'

Antisense primer (SEQ ID NO: 48)

3'-ACA CAA CAA CCG ATG CTA CCG CTC GCA ACG GTC-5'

(10) Substitution of CGT, codon of 41$^{st}$ arginine, with TGC, codon of cysteine, in SEQ ID NO: 1

Sense primer (SEQ ID NO: 49)

5'-GGC TAC ATC GGC GAG TGC TGC CAG TAT CGT GAC-3'

Antisense primer (SEQ ID NO: 50)

3'-CCG ATG TAG CCG CTC ACG ACG GTC ATA GCA CTG-5'

(11) Substitution of GAC, codon of 46<sup>th</sup> aspartic acid, with TGC, codon of cysteine, in SEQ ID NO: 1

Sense primer (SEQ ID NO: 51)
5'-CGT TGC CAG TAT CGT TGC CTG AAA TGG TGG GAA-3'

Antisense primer (SEQ ID NO: 52)
3'-GCA ACG GTC ATA GCA ACG GAC TTT ACC ACC CTT-5'

(12) Substitution of AAA, codon of 48<sup>th</sup> lysine, with CGT, codon of arginine, in SEQ ID NO: 1

Sense primer (SEQ ID NO: 53)
5'-CAG TAT CGT GAC CTG AAA TGG TGG GAA CTG CGC-3'

Antisense primer (SEQ ID NO: 54)
3'-GTC ATA GCA CTG GAC TTT ACC ACC CTT GAC GCG-5'

(13) Substitution of TGG, codon of 50<sup>th</sup> tryptophan, with AGC, codon of serine, CAT, codon of histidine, or GAA, codon of glutamic acid, in SEQ ID NO: 1

Sense primer (SEQ ID NO: 55)
5'-CAG TAT CGT GAC CTG AAA AGC TGG GAA CTG CGC-3'

Antisense primer (SEQ ID NO: 56)
3'-GTC ATA GCA CTG GAC TTT TCG ACC CTT GAC GCG-5'

Sense primer (SEQ ID NO: 57)
5'-CAG TAT CGT GAC CTG AAA CAT TGG GAA CTG CGC-3'

Antisense primer (SEQ ID NO: 58)
3'-GTC ATA GCA CTG GAC TTT GTA ACC CTT GAC GCG-5'

Sense primer (SEQ ID NO: 59)
5'-CAG TAT CGT GAC CTG AAA GAA TGG GAA CTG CGC-3'

Antisense primer (SEQ ID NO: 60)
3'-GTC ATA GCA CTG GAC TTT CTT ACC CTT GAC GCG-5'

Example 4

Production and Purification of EGF Mutant

The stocks were prepared by transforming *E. coli* BL21 (DE3) with the respective expression plasmids of the EGF mutants as listed in Table 1, using the same method as Example 2. The stocks were cultured in 500 ml of LB medium (LB/ampicillin), and purified to obtain the respective EGFs having about 6 KDa size. At this time, the amount of human tumor necrosis factor mutant was depended on the mutants, and about 0.3 to 0.5 mg of the EGF was obtained according to the mutants and the purities thereof were 98% or higher.

TABLE 1

| | Region 1 (A) | Region 2 (B) | Region 3 (C) | Region 4 (D) | Region 5 (E) |
|---|---|---|---|---|---|
| Amino acid No. (SEQ ID NO: 1) | 1~10 | 11~20 | 21~30 | 31~40 | 41~53 |
| Wild-type EGF sequence | N S D S E C P L S H (SEQ ID NO: 61) | D G Y C L H D G V C (SEQ ID NO: 65) | M Y I E A L D K Y A (SEQ ID NO: 71) | C N C V V G Y I G E (SEQ ID NO: 74) | R C Q Y R D L K W W E L R (SEQ ID NO: 87) |

TABLE 1-continued

| Mutant EGF name (region-site) | Region 1 (A) Region 1 sequence | Region 2 (B) Region 2 sequence | Region 3 (C) Region 3 sequence | Region 4 (D) Region 4 sequence | Region 5 (E) Region 5 sequence |
|---|---|---|---|---|---|
| A-4-1 | N S D E _E_ C P L S H (SEQ ID NO: 62) | — | — | — | — |
| A-8-2 | N S D S E C P _S_ S H (SEQ ID NO: 63) | — | — | — | — |
| A-8-3 | N S D S E C P _P_ S H (SEQ ID NO: 64) | — | — | — | — |
| B-15-1 | — | D G Y C C H D G V C (SEQ ID NO: 66) | — | — | — |
| B-19-2 | — | D G Y C L H D G S C (SEQ ID NO: 67) | — | — | — |
| B-19-3 | — | D G Y C L H D G E C (SEQ ID NO: 68) | — | — | — |
| B-19-4 | — | D G Y C L H D G D C (SEQ ID NO: 69) | — | — | — |
| B-19-5 | — | D G Y C L H D G K C (SEQ ID NO: 70) | — | — | — |
| C-25-1 | — | — | M Y I E S L D K Y A (SEQ ID NO: 72) | — | — |
| C-26-2 | — | — | M Y I E A S D K Y A (SEQ ID NO: 73) | — | — |
| D-34-1 | — | — | — | C N C S V G Y I G E (SEQ ID NO: 75) | — |
| D-34-2 | — | — | — | C N C E V G Y I G E (SEQ ID NO: 76) | — |
| D-34-3 | — | — | — | C N C D V G Y I G E (SEQ ID NO: 77) | — |
| D-34-4 | — | — | — | C N C K V G Y I G E (SEQ ID NO: 78) | — |
| D-35-5 | — | — | — | C N C V S G Y I G E (SEQ ID NO: 79) | — |
| D-35-6 | — | — | — | C N C V E G Y I G E (SEQ ID NO: 80) | — |
| D-35-7 | — | — | — | C N C V D G Y I G E (SEQ ID NO: 81) | — |

TABLE 1-continued

| | Region 1 (A) | Region 2 (B) | Region 3 (C) | Region 4 (D) | Region 5 (E) |
|---|---|---|---|---|---|
| D-35-8 | — | — | — | C N C V K G Y I G E (SEQ ID NO: 82) | — |
| D-38-9 | — | — | — | C N C V V G Y S G E (SEQ ID NO: 83) | — |
| D-38-10 | — | — | — | C N C V V G Y C G E (SEQ ID NO: 84) | — |
| D-38-11 | — | — | — | C N C V V G Y E G E (SEQ ID NO: 85) | — |
| D-38-12 | — | — | — | C N C V V G Y <u>D</u> G E (SEQ ID NO: 86) | — |
| E-41-1 | — | — | — | — | C C Q Y R D L K W W E L R (SEQ ID NO: 88) |
| E-46-2 | — | — | — | — | R C Q Y R C L K W W E L R (SEQ ID NO: 89) |
| E-48-3 | — | — | — | — | R C Q Y R D L R W W E L R (SEQ ID NO: 90) |
| E-50-4 | — | — | — | — | R C Q Y R D L K W S E L R (SEQ ID NO: 91) |
| E-50-5 | — | — | — | — | R C Q Y R D L K W H E L R (SEQ ID NO: 92) |
| E-50-6 | — | — | — | — | R C Q Y R D L K W E E L R (SEQ ID NO: 93) |
| *M1 | — | D G Y C C H D G V C (SEQ ID NO: 66) | — | — | C C Q Y R D L K W W E L R (SEQ ID NO: 94) |
| *M2 | — | — | — | C N C V V G Y C G E (SEQ ID NO: 84) | R C Q Y R C L K W W E L R (SEQ ID NO: 95) |
| *M3 | N S D S E C P <u>S</u> S H (SEQ ID NO: 63) | — | — | C N C V V G Y C G E (SEQ ID NO: 84) | R C Q Y R C L K W W E L R (SEQ ID NO: 96) |

*M1 was a mutant prepared by fusion of B-15-1 and E-41-1, M2 was a mutant by fusion of D-38-10 and E-46-2, and M3 was a mutant by fusion of A-8-2, D-38-10, and E-46-2.

*M1 was a mutant prepared by fusion of B-15-1 and E-41-1, M2 was a mutant by fusion of D-38-10 and E-46-2, and M3 was a mutant by fusion of A-8-2, D-38-10, and E-46-2.

Example 5

Analysis of Solubility of Wild-Type and Mutant EGFs 1 mg of the respective wild-type and mutant EGFs prepared was dissolved in 1 ml of 20 mM sodium phosphate (pH 5.5 that is the similarly pH environment as cosmetics). In order to remove undissolved EGF, the mixture thus obtained was centrifuged and then supernatant was obtained. The concentration of the supernatant thus obtained was measured by using a Bradford method and UV method.

TABLE 2

| Mutant EGF name | Solubility, mg/ml (Comparison with wild-type %) | Mutant EGF name | Solubility, mg/ml (Comparison with wild-type %) | Mutant EGF name | Solubility, mg/ml (Comparison with wild-type %) |
|---|---|---|---|---|---|
| Wild-type EGF | 0.5073 (100) | D-34-1 | | D-38-12 | |
| A-4-1 | | D-34-2 | 0.5741 (113) | E-41-1 | N/A |
| A-8-2 | 0.6991 (137) | D-34-3 | | E-46-2 | N/A |
| A-8-3 | | D-34-4 | | E-48-3 | |
| B-15-1 | N/A | D-35-5 | | E-50-4 | |
| B-19-2 | | D-35-6 | 0.5328 (105) | E-50-5 | |
| B-19-3 | 0.4822 (95) | D-35-7 | | E-50-6 | |
| B-19-4 | | D-35-8 | | M1 | 0.4032 (79) |
| B-19-5 | | D-38-9 | 0.4972 (98) | M2 | 0.4260 (84) |
| C-25-1 | 0.6178 (122) | D-38-10 | N/A | M3 | 0.6817 (134) |
| C-26-2 | | D-38-11 | | | |

As listed in Table 2, most wild-type EGFs have the similar solubility of 0.5 mg/ml, and the EGF mutants of A-8-2, C-25-1, and M3 have about 20 to 40% higher solubility than the wild-type EGF. From the above results, it can be confirmed that the present invention is excellent, because the solubility is increased by strengthening hydrophilic property through a method of changing hydrophobic residues with hydrophilic residues on the surface. In cases of M1 and M2, the solubility is decreased as compared with the wild-type EGF by further adding a disulfide bond.

Example 6

Analysis of Structure of Wild-Type and Mutant EGFs Using Circular Dichroism

The structure and thermal stability of the purified EGF mutant were measured through a circular dichroism analysis using a J-810 spectrometer (JASCO). As the wild-type EGF, the purified EGF prepared in Example 2 was used. In order to analyze the structure, each EGF was dissolved in 20 mM sodium phosphate (pH 5.5) to be uniformly a final concentration of 0.1 mg/ml. And then, the dissolved EGF solution was added to 0.1 cm cell, and then its structure was analyzed under the conditions of, as 190 nm to 250 nm region, band width 1 nm, response 0.25 sec, data pitch 0.1 nm, scanning speed 20 nm/min, cell length 1 cm, accumulation 8 times, and a temperature of 20° C.

In order to analyze the thermal stability, a wavelength of 200 nm was determined through a comparison analysis of far-UV at the Tm (melting temperature) of 20° C. and 95° C., and progressed in a concentration of 0.1 mg/ml in 0.1 cm cell. As the conditions, it was measured at 20° C. to 95° C. under condition of 1° C./min.

TABLE 3

| Mutant EGF name | Structure change (Tm) | Mutant EGF name | Structure change (Tm) | Mutant EGF name | Structure change (Tm) |
|---|---|---|---|---|---|
| Wide type EGF | — (76° C.) | D-34-1 | No change (76° C.) | D-38-12 | No change (76° C.) |
| A-4-1 | No change (76° C.) | D-34-2 | No change (76° C.) | E-41-1 | N/A |
| A-8-2 | No change (76° C.) | D-34-3 | No change (76° C.) | E-46-2 | N/A |
| A-8-3 | No change (76° C.) | D-34-4 | No change (76° C.) | E-48-3 | No change (76° C.) |
| B-15-1 | N/A | D-35-5 | No change (76° C.) | E-50-4 | No change (76° C.) |
| B-19-2 | No change (76° C.) | D-35-6 | No change (76° C.) | E-50-5 | No change (76° C.) |
| B-19-3 | No change (76° C.) | D-35-7 | No change (76° C.) | E-50-6 | No change (76° C.) |
| B-19-4 | No change (76° C.) | D-35-8 | No change (76° C.) | M1 | No structure (—) |
| B-19-5 | No change (76° C.) | D-38-9 | No change (76° C.) | M2 | Little change (87° C.) |
| C-25-1 | No change (76° C.) | D-38-10 | N/A | M3 | Little change (87° C.) |
| C-26-2 | No change (76° C.) | D-38-11 | No change (76° C.) | | |

Table 3 exhibits values exhibiting the results for measuring fraction unfolded per temperature at a wavelength of 195 nm during a circular dichroism analysis for measuring a degree of structure change and thermal stability about a wild-type EGF and EGF mutants. The structure is changed at the band of about 195 nm when generating a folding-unfolding phenomenon. Using it, the melting temperature (Tm) was measured in the range of 20 to 95° C., and thus the accurate Tm value was analyzed. As a result, as for the structure change, most mutants had the similar structure as the wild-type EGF, and thus there were few changes. M1 further added with a disulfide bond didn't have such a specific structure, and M2 and M3 had the structure that was slightly changed as compared with the wild-type EGF. As for Tm exhibiting the degree of thermal stability, most EGF mutants had the same Tm as compared with the wild-type EGF that had Tm of 76° C. It can be confirmed that the thermal stabilities of M2 and M3 were improved by 87° C. From the above result, it can be confirmed that the superiority of the present invention is proved, because the thermal stability is increased by further adding a disulfide bond by substituting two amino acids with cysteine, respectively, which is desired by us.

Example 7

Test of Cell Proliferations of Wild-Type and Mutant EGFs

Among the prepared wild-type EGFs and mutants, some EGFs and mutants exhibiting the good results were selected through the analysis of the results of Tm and structures obtained from solubility and circular dichroism, and then subjected to the test of cell proliferation. The test of cell proliferation was performed by InnoPharmaScreen, Inc. They performed with NIH3T3 cell line that is a skin cell susceptible to EGF. As a test method, NIH-3T3 cell was maintained by using a DMEM complete medium including fetal bovine serum subjected to 10% heat-inactivation, 100 units/ml of penicillin, and 100 mg/ml of streptomycin. $2 \times 10^3$ cells/well of NIH-3T3 cell was seeded to 96 well culture plate. The NIH-3T3 cell cultured for 24 hours was subjected to starvation using a serum-free DMEM medium. Since then, each of the sample solutions having different concentrations was treated to a DMEM medium including 0.5% FBS, and then cultured for 72 hours. After culturing, 10 μl of MTT [3-(4,5-dimethylthiazol-2-yl)-2,5-diphenyl-2H-tetrazolium bromide] solution was added to the cultured cells, and then cultured for 2 hours. Since then, the formazan crystal was dissolved with 100 μl of DMSO. The Absorbance was measured at a wavelength of 540 nm using a spectrophotometer. As for sensitivity to chemicals, the percentages of the well treated with chemicals to the absorbance of the well not treated with chemicals (Control) were compared. As can be seen in FIG. 2A-D, most EGF mutants exhibit the similar cell proliferation ability as the wild-type EGF, and M1 not having the structure does not exhibit the cell proliferation ability.

Example 8

Figure 3:
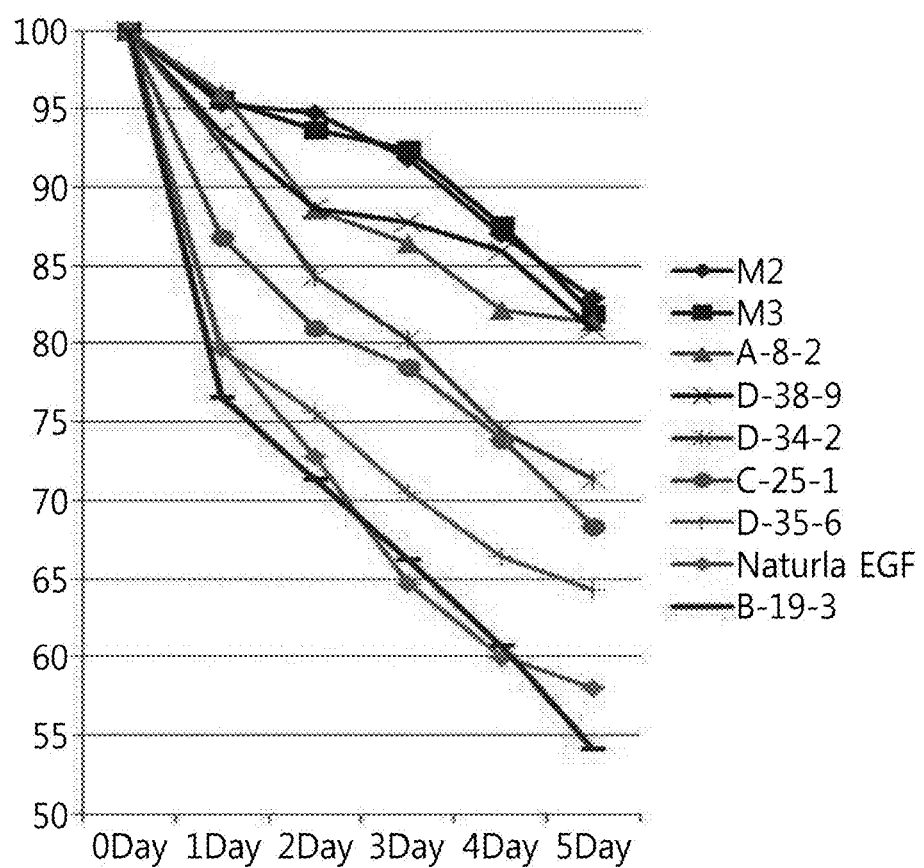
FIG. 3 is a graph exhibiting the structures measured by using a circular dichroism after sampling per 24 hours while the wild-type EGF and EGF mutant are reacted at a temperature of 60° C. and 20 mM sodium phosphate (pH 5.5). And then, the percentage was obtained using the ratio with the signal value at a first day using the signal value of 200 nm that has the biggest difference of signal, and then exhibited as a graph. The signal of wild-type EGF was significantly decreased as compared with that of the EGF mutants.

Analysis of Circular Dichroism According to Incubation of Wild-Type and Mutant EGFs The stabilities of wild-type EGF and mutants should be confirmed through being stored at room temperature for a long period of time, but there is a disadvantage in that the time is too long. Therefore, the incubation test was performed at extreme environment for a short period of time. 0.3 mg/ml of each of the wild-type EGF and mutants was dissolved in 20 mM sodium phosphate (pH 5.5), and then subjected to the incubation in a water bath of 60° C. The sampling was performed per 24 hours unit, and then centrifuged at 13000 rpm and 4° C. for 15 minutes to collect the supernatant. The supernatant was diluted with 20 mM sodium phosphate (pH 5.5), and its structure was measured by using a circular dichroism. And then, the supernatant was added to 0.1 cm cell, and its structure was analyzed under the conditions of, in a region of 190 nm to 250 nm, band width 1 nm, response 0.25 sec, data pitch 0.1 nm, scanning speed 20 nm/min, cell length 1 cm, accumulation 8 times, a temperature of 20° C. Over time, the structure signal of the wild-type EGF mutants was decreased, and the signal of the wild-type EGF was significantly decreased as compared with the mutants. In order to easily confirm such a result, the graph as illustrated in FIG. 3 is used using the ratio of the signal value at a first day to the signal value at 200 nm that has the biggest difference of signals. Table. 4 shows the percentage when the signal value of the wild-type EGF at five days was compared with the signal value of the mutants. The A-8-2, D-38-9, M2, and M3 mutants exhibit about 125% signal value as compared with the wild-type EGF. From such a result, it can be confirmed that the EGF mutants prepared in the present invention have excellent thermal stability and solubility.

TABLE 4

| Mutant EGF name | Percentage to wild-type EGF (%) | Mutant EGF name | Percentage to wild-type EGF (%) |
| --- | --- | --- | --- |
| Wild-type EGF | 100 | D-34-2 | 111.10 |
| M2 | 129.13 | C-25-1 | 106.38 |
| M3 | 127.48 | D-35-6 | 100.14 |
| A-8-2 | 126.68 | B-19-3 | 84.22 |
| D-38-9 | 125.93 | | |

Example 9

Figure 4:
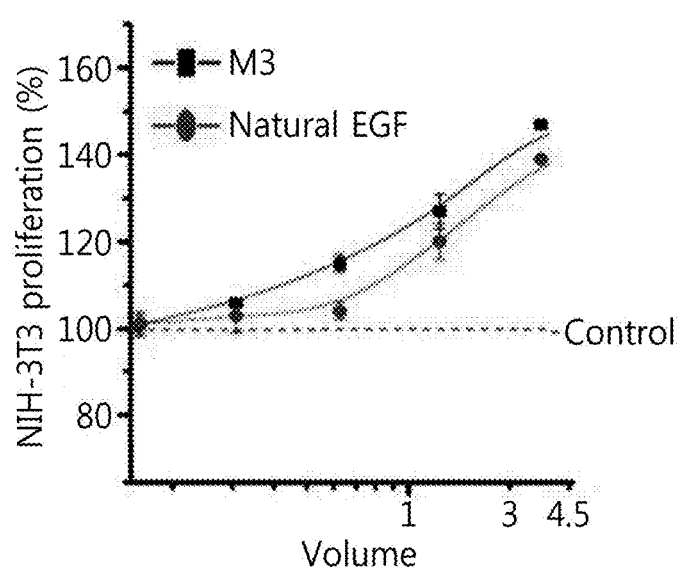
FIG. 4 is a graph comparing the abilities of cell proliferation between the wild-type EGF and EGF mutant after reacting for 5 days in the state of 60° C. and cosmetic basic essence, in which the EGF mutant exhibits the higher ability of cell proliferation as compared with the wild-type EGF.

Test of Cell Proliferation According to Incubation of Wild-Type EGF and M3 Mutant Based on the above-mentioned results, with the M3 mutant that exhibited the best solubility and the thermal stability, in order to confirm whether or not the M3 mutant has the thermal stability as compared with the wild-type EGF even in the state of the real cosmetics, not in the state of 20 mM sodium phosphate (pH 5.5), the wild-type EGF and M3 mutant in the state of the cosmetic basic essence were dissolved in the same concentration, and then incubated at a temperature of 60° C. for 5 days. And then, the incubated samples were centrifuged to collect supernatants. The test of cell proliferation was performed with NIH3T3 cell line that is a skin cell susceptible to an EGF by InnoPharmaScreen, Inc. As can be seen in FIG. 4, it can be confirmed that the M3 mutant exhibits the higher cell proliferation activity as compared with the wild-type EGF. From such a result, it can be confirmed that since the M3 mutant exhibits the higher thermal stability and solubility as compared with the wild-type EGF, the superiority of the present invention is proved.

The present invention relates to a highly stabilized epidermal growth factor (EGF) mutant, in which the activity of the EGF mutant is maintained while the thermal stability and solubility in an aqueous solution thereof are increased by using a substitution method with a disulfide bond and hydrophilic residues. By preparing a product using the EGF mutant according to the present invention, it is possible to produce functional cosmetics, in which the activity thereof is maintained even during a distribution and storage process unlike the conventional wild-type EGF product.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:
1. A mutant epidermal growth factor (EGF) protein, comprising an amino acid sequence as set forth in SEQ ID NO:2.

* * * * *

SEQUENCE LISTING

```
<160> NUMBER OF SEQ ID NOS: 96

<210> SEQ ID NO 1
<211> LENGTH: 53
<212> TYPE: PRT
<213> ORGANISM: Homo sapiens

<400> SEQUENCE: 1

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 53
<212> TYPE: PRT
<213> ORGANISM: Artificial Sequence
<220> FEATURE:
<223> OTHER INFORMATION: Description of Artificial Sequence: Synthetic
      epidermal growth factor(EGF) polypeptide mutant

<400> SEQUENCE: 2

Asn Ser Asp Ser Glu Cys Pro Ser Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Cys Gly Glu Arg Cys Gln Tyr Arg Cys Leu Lys
        35                  40                  45

Trp Trp Glu Leu Arg
    50

<210> SEQ ID NO 3
<211> LENGTH: 159
<212> TYPE: DNA
<213> ORGANISM: Homo sapiens

<400> SEQUENCE: 3
aacagcgata gcgaatgccc gctgagccat gatggctatt gcctgcatga tggtgtgtgc      60
atgtatattg aagcattgga caagtatgca tgcaactgtg ttgttggcta catcggcgag     120
cgttgccagt atcgtgacct gaaatggtgg gaactgcgc                            159

<210> SEQ ID NO 4
<211> LENGTH: 159
<212> TYPE: DNA
<213> ORGANISM: Artificial Sequence
<220> FEATURE:
<223> OTHER INFORMATION: Description of Artificial Sequence: Synthetic
      epidermal growth factor(EGF) polynucleotide mutant

<400> SEQUENCE: 4
aacagcgata gcgaatgccc gagcagccat gatggctatt gcctgcatga tggtgtgtgc      60
```

```
atgtatattg aagcattgga caagtatgca tgcaactgtg ttgttggcta ctgcggcgag    120
cgttgccagt atcgttgcct gaaatggtgg gaactgcgc                           159
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
gctgttcata tgaacagcga tagcgaatgc                                      30
```

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
accacccttg acgcgattat tttcgaaaat aat                                  33
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
aacagcgatg aagaatgccc gctgagc                                         27
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gctcagcggg cattcttcat cgctgtt                                         27
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gatagcgaat gcccgagcag ccatgatggc tat                                  33
```

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 10
atagccatca tggctgctcg ggcattcgct atc                                33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catgatggct attgctgcca tgatggtgtg tgc                                33

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcacacacca tcatggcagc aatagccatc atg                                33

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgcctgcatg atggtagctg catgtatatt gaa                                33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttcaatatac atgcagctac catcatgcag gca                                33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgcctgcatg atggtgaatg catgtatatt gaa                                33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
```
ttcaatatac atgcattaac catcatgcag gca                            33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgcctgcatg atggtgattg catgtatatt gaa                            33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ttcaatatac atgcaatcac catcatgcag gca                            33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgcctgcatg atggtaaatg catgtatatt gaa                            33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttcaatatac atgcatttac catcatgcag gca                            33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcatgtata ttgaaagctt ggacaagtat gca                            33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcatacttg tccaagcttt caatatacat gca                                33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgtatattg aaagcttgga caagtatgca tgc                                33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcatgcatac ttgtccaagc tttcaatata cat                                33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tatgcatgca actgtagcgt tggctacatc ggc                                33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccgatgtag ccaacgctac agttgcatgc ata                                33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tatgcatgca actgtgaagt tggctacatc ggc                                33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gccgatgtag ccaacttcac agttgcatgc ata                                33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tatgcatgca actgtgatgt tggctacatc ggc                33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gccgatgtag ccaacatcac agttgcatgc ata                33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tatgcatgca actgtaaagt tggctacatc ggc                33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gccgatgtag ccaactttac agttgcatgc ata                33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gcatgcaact gtgttagcgg ctacatcggc gag                33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ctcgccgatg tagccgctaa cacagttgca tgc                33

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcatgcaact gtgttgaagg ctacatcggc gag                                   33

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctcgccgatg tagccttcaa cacagttgca tgc                                   33

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcatgcaact gtgttgatgg ctacatcggc gag                                   33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctcgccgatg tagccatcaa cacagttgca tgc                                   33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcatgcaact gtgttaaagg ctacatcggc gag                                   33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctcgccgatg tagcctttaa cacagttgca tgc                                   33

-continued

```
<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtgttgttg gctacagcgg cgagcgttgc cag                                  33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctggcaacgc tcgccgctgt agccaacaac aca                                  33

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgtgttgttg gctactgcgg cgagcgttgc cag                                  33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctggcaacgc tcgccgcagt agccaacaac aca                                  33

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgtgttgttg gctacgaagg cgagcgttgc cag                                  33

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctggcaacgc tcgccttcgt agccaacaac aca                                  33

<210> SEQ ID NO 47
```

<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tgtgttgttg gctacgatgg cgagcgttgc cag                33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ctggcaacgc tcgccatcgt agccaacaac aca                33

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ggctacatcg gcgagtgctg ccagtatcgt gac                33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gtcacgatac tggcagcact cgccgatgta gcc                33

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
cgttgccagt atcgttgcct gaaatggtgg gaa                33

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ttcccaccat ttcaggcaac gatactggca acg                33

<210> SEQ ID NO 53
<211> LENGTH: 33

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cagtatcgtg acctgaaatg gtgggaactg cgc                                    33

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcgcagttcc caccatttca ggtcacgata ctg                                    33

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cagtatcgtg acctgaaaag ctgggaactg cgc                                    33

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcgcagttcc cagcttttca ggtcacgata ctg                                    33

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cagtatcgtg acctgaaaca ttgggaactg cgc                                    33

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcgcagttcc caatgtttca ggtcacgata ctg                                    33

<210> SEQ ID NO 59
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 59
cagtatcgtg acctgaaaga atgggaactg cgc                                   33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcgcagttcc cattctttca ggtcacgata ctg                                   33

<210> SEQ ID NO 61
<211> LENGTH: 10
<212> TYPE: PRT
<213> ORGANISM: Homo sapiens

<400> SEQUENCE: 61

Asn Ser Asp Ser Glu Cys Pro Leu Ser His
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Ser Asp Glu Glu Cys Pro Leu Ser His
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Ser Asp Ser Glu Cys Pro Ser Ser His
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Ser Asp Ser Glu Cys Pro Pro Ser His
1               5                   10

<210> SEQ ID NO 65
<211> LENGTH: 10
<212> TYPE: PRT
```

```
<213> ORGANISM: Homo sapiens

<400> SEQUENCE: 65

Asp Gly Tyr Cys Leu His Asp Gly Val Cys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Gly Tyr Cys Cys His Asp Gly Val Cys
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Gly Tyr Cys Leu His Asp Gly Ser Cys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Gly Tyr Cys Leu His Asp Gly Glu Cys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Gly Tyr Cys Leu His Asp Gly Asp Cys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Gly Tyr Cys Leu His Asp Gly Lys Cys
1               5                   10

<210> SEQ ID NO 71
```

```
<211> LENGTH: 10
<212> TYPE: PRT
<213> ORGANISM: Homo sapiens

<400> SEQUENCE: 71

Met Tyr Ile Glu Ala Leu Asp Lys Tyr Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Tyr Ile Glu Ser Leu Asp Lys Tyr Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met Tyr Ile Glu Ala Ser Asp Lys Tyr Ala
1               5                   10

<210> SEQ ID NO 74
<211> LENGTH: 10
<212> TYPE: PRT
<213> ORGANISM: Homo sapiens

<400> SEQUENCE: 74

Cys Asn Cys Val Val Gly Tyr Ile Gly Glu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Asn Cys Ser Val Gly Tyr Ile Gly Glu
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Cys Asn Cys Glu Val Gly Tyr Ile Gly Glu
1               5                   10

<210> SEQ ID NO 77
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Asn Cys Asp Val Gly Tyr Ile Gly Glu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Asn Cys Lys Val Gly Tyr Ile Gly Glu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Asn Cys Val Ser Gly Tyr Ile Gly Glu
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Cys Asn Cys Val Glu Gly Tyr Ile Gly Glu
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Asn Cys Val Asp Gly Tyr Ile Gly Glu
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Asn Cys Val Lys Gly Tyr Ile Gly Glu
```

```
1               5                   10
```

```
<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Asn Cys Val Val Gly Tyr Ser Gly Glu
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Cys Asn Cys Val Val Gly Tyr Cys Gly Glu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Asn Cys Val Val Gly Tyr Glu Gly Glu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Asn Cys Val Val Gly Tyr Asp Gly Glu
1               5                   10

<210> SEQ ID NO 87
<211> LENGTH: 13
<212> TYPE: PRT
<213> ORGANISM: Homo sapiens

<400> SEQUENCE: 87

Arg Cys Gln Tyr Arg Asp Leu Lys Trp Trp Glu Leu Arg
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

Cys Cys Gln Tyr Arg Asp Leu Lys Trp Trp Glu Leu Arg
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Cys Gln Tyr Arg Cys Leu Lys Trp Trp Glu Leu Arg
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Cys Gln Tyr Arg Asp Leu Arg Trp Trp Glu Leu Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Cys Gln Tyr Arg Asp Leu Lys Trp Ser Glu Leu Arg
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Cys Gln Tyr Arg Asp Leu Lys Trp His Glu Leu Arg
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Cys Gln Tyr Arg Asp Leu Lys Trp Glu Glu Leu Arg
1               5                   10

<210> SEQ ID NO 94
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 94

Cys Cys Gln Tyr Arg Asp Leu Lys Trp Trp Glu Leu Arg
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Cys Gln Tyr Arg Cys Leu Lys Trp Trp Glu Leu Arg
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Cys Gln Tyr Arg Cys Leu Lys Trp Trp Glu Leu Arg
1               5                   10
```